US00PP17752P2

(12) United States Plant Patent
van Zanten

(10) Patent No.: US PP17,752 P2
(45) Date of Patent: May 22, 2007

(54) ***CHRYSANTHEMUM* PLANT NAMED 'GGX 1084'**

(50) Latin Name: *Chrysanthemum grandiflora*
Varietal Denomination: GGX 1084

(75) Inventor: Leo van Zanten, Oxnard, CA (US)

(73) Assignee: Grolink Corporation, Oxnard, CA (US)

( * ) Notice: Subject to any disclaimer, the term of this patent is extended or adjusted under 35 U.S.C. 154(b) by 0 days.

(21) Appl. No.: 11/236,975

(22) Filed: Sep. 28, 2005

(51) Int. Cl.
*A01H 5/00* (2006.01)

(52) U.S. Cl. ..... Plt./297
(58) Field of Classification Search ..... Plt./297
See application file for complete search history.

*Primary Examiner*—Anne Marie Grunberg
*Assistant Examiner*—Georgia Helmer

(57) ABSTRACT

A new and distinct *Chrysanthemum* plant cultivar is disclosed, characterized by large daisy type inflorescences, consistent flowering response to short days, blooming consistently after 50 to 55 days of short day length, bi color orange and yellow ray florets, moderate to compact growth habit and a postharvest longevity of an average of 35 days.

1 Drawing Sheet

Latin name of the genus and species: *Chrysanthemum grandiflora. 'GGX* 1084'.

BACKGROUND OF THE INVENTION

The new cultivar 'GGX 1084' is a product of a naturally occurring, single branch mutation of the parent *Chrysanthemum* plant variety 'GGX 001'(not patented) which is an undistributed proprietary cultivar. The new cultivar was discovered and selected by Leo van Zanten in March 2003 in Carpinteria, Calif.

Asexual reproduction of the new cultivar 'GGX 1084' by terminal cuttings and tissue culture was performed in Oxnard Calif. and Carpinteria Calif., and has shown that the unique features of this new cultivar are stable and reproduced true to type on successive generations.

SUMMARY OF THE INVENTION

The cultivar 'GGX 1084' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GGX 1084.' These characteristics in combination distinguish 'GGX 1084' as a new and distinct *Chrysanthemum* cultivar:

1. Large daisy type inflorescence;
2. Consistent flowering response to short days, blooming consistently after 47 to 49 days of short day length;
3. Upright branching habit
4. Pink ray florets
5. Light green center disc coloration Plants of the new cultivar 'GGX 1084'are similar to plants of the parent variety, 'GGX 001' in most horticultural characteristics, however plants of the new cultivar 'GGX 1084' differ in the following characteristics:

1. Shorter blooming response, the new cultivar blooms consistently 3 days earlier
2. More ray florets 3. Disc coloration is more green in the new variety
4. Better post production longevity
5. More branches on average produced from a pinch In comparison to the commercially available variety 'Reagan' (U.S. Plant Pat. No. 8,642.), 'GGX 1084' differs in the following characteristics:

1. The new cultivar has a shorter blooming response by 5 days
2. The new cultivar has a more consistent ray floret coloration under high light and high temperatures
3. The new cultivar resists disc floret discoloration with age.
4. The cultivar is shorter by at least 10 to 20 cm when grown side by side.
5. The new cultivar has a distinctive green center disc coloration, which resists changing color with aging of the plant.
6. The new cultivar has a longer vase life by approximately 5 days.

BRIEF DESCRIPTION OF THE PHOTOGRAPH

The accompanying photograph in FIG. 1 illustrates a close up of the flowers and buds of an 11 week old plant of 'GGX 1084,' showing the consistent ray floret coloration at various ages of flowers. Plants producing flowers for the photograph were grown in a commercial greenhouse with day temperatures average 15 to 28 deg. C. and night temperatures average 15 to 18 deg C.

DETAILED BOTANICAL DESCRIPTION

In the following description, color references are made to The Royal Horticultural Society Colour Chart except where general terms of ordinary dictionary significance are used. The following observations and measurements describe 'GGX 1084' plants grown in Oxnard, Ventura County, Calif., during the months of August through October 2004. The plants were 11 weeks old. The growing temperature ranged from 15° C. to 18° C. at night to 15° C. to 28° C.

during the day. Measurements and numerical values represent averages of typical flowering types.

Botanical classification: *Chrysanthemum grandiflora* cultivar 'GGX 1084.'
Commercial classification: Cut flower-type *Chrysanthemum.*

PROPAGATION

Time to rooting: 7 to 14 days at approximately 21° C.
Root description: Fine, fibrous.

PLANT

Growth habit: Upright.
Height: Approximately 80 to 90 cm.
Plant spread: Approximately 25 to 35 cm.
Growth rate: Moderate.
Branching characteristics: Moderate upright branching.
Length of lateral branches: Approximately 70 to75 cm.
Number of leaves per lateral branch: Approximately 30 to 40.
Age of plant described: Approximately 50 days.

FOLIAGE

Leaf:
*Arrangement.*—Alternate single.
*Average length.*—Approximately 9.7 cm.
*Average width.*—Approximately 7.8 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 3 cm.
*Color.*—Young foliage upper side: Near Green 137C. Young foliage under side: Near Green 138B. Mature foliage upper side: Near Green 137A. Mature foliage under side: Near Green 137B.
*Venation.*—Type: Palmately net. Venation color upper side: Near Yellow-Green 146B. Venation color under side: Near Green 137D.
Petiole:
*Average length.*—Approximately 1.9 cm.
*Color.*—Near Green 137C.
*Diameter.*—Approximately 0.6 cm.

BLOOM

Inflorescence:
*Flowering habit.*—Induced by darkness period greater than 13.5 hours, approximately 47 days of appropriate day length required to induce and develop blooms.
*Inflorescence form.*—Daisy.
*Number of inflorescences per lateral branch.*—Approximately 12.
*Inflorescence diameter.*—Approximately 5.7 cm.
*Inflorescence depth.*—Approximately 2.5 cm.
*Disc diameter.*—Approximately 1.2 cm.
*Inflorescence longevity in vase.*—Approximately 30 to 32 days.
*Persistence.*—Persistent.
Ray florets:
*Appearance.*—Matte.
*Texture.*—Smooth.
*Average number of ray florets per inflorescence.*—Approximately 20 to 25.
*Shape.*—Oblanceolate.
*Aspect.*—Flat.
*Margin.*—Entire.
*Apex.*—Obtuse.
*Length.*—Approximately 1.8 cm.
*Width.*—Approximately 0.8 cm.
*Color.*—Upper surface at first opening: Near Red-Purple 62C. Upper surface at maturity: Near Red-Purple 62D. Upper surface at fading: Near Red-Purple 65D. Under surface at first opening: Near Orange 27A tips with Red 54D base. Under surface at maturity: Near Red 56C. Under surface at fading: Near Red 56D.
Disc florets:
*Appearance.*—Shiny.
*Texture.*—Smooth.
*Average number of florets per disc.*—Approximately 350.
*Shape.*—Cylindric.
*Apex.*—Obtuse.
*Average length.*—Approximately 0.7 cm.
*Average width.*—Approximately 0.1 cm.
*Color.*—At first opening: Near Green 143C. At maturity: Near Green-Yellow 1A. At fading: Near Yellow 6C.
Peduncle:
*Length.*—At terminal end (shortest): Approximately 7 cm. At lateral end (longest): Approximately 20 cm.
*Angle to stem.*—Acute.
*Strength.*—Moderate.
*Color.*—Near Green 137B.
*Habit.*—Upright.
*Diameter.*—0.5 cm.
*Surface texture.*—Lightly pubescent.
Inflorescence bud:
*Length.*—Approximately 1.2 cm.
*Diameter.*—Approximately 1 cm.
*Form.*—Globular.
*Color.*—Near Yellow 6B.
Involucral bracts (phyllaries):
*Appearance.*—Matte.
*Texture.*—Lightly pubescent.
*Number.*—Approximately 15.
*Shape.*—Ovate.
*Margin.*—Entire.
*Apex.*—Acute.
*Length.*—1 cm.
*Width.*—1.1 cm.
*Color.*—Upper side: Near Green 137B. Under side: Near Green 137B.

REPRODUCTIVE ORGANS

Ray florets:
*Number of pistils per floret.*—1.
*Stigma shape.*—2 branched.
*Stigma color.*—Near 15A.
*Style color.*—Near Yellow 7A.
*Style length.*—Approximately 1 cm.
*Stamens.*—Absent.
Disc florets:
*Number of pistils per floret.*—1.
*Stigma shape.*—Cylindric.
*Stigma color.*—Near 154A.

*Style length.*—Approximately 0.2 cm.
*Style color.*—Near Yellow-Green 154A.
*Number of stamens per floret.*—Approximately 5.
*Anther shape.*—Tubular.
*Anther color.*—Near Yellow 2A.
*Pollen color.*—Near Yellow 6A.

OTHER CHARACTERISTICS

Disease resistance: Neither resistance nor susceptibility to diseases or pests has been observed in this variety.

Drought tolerance cold/tolerance: The new cultivar has only been observed under indoor conditions, therefore drought and cold tolerance have not been observed.

Fruit/seed production: Commercially, this plant is not used or observed in a stage where seeds would be produced. Therefore, seed production has not been observed.

What is claimed is:

1. A new and distinct cultivar of *Chrysanthemum* plant named 'GGX 1084' as illustrated and described.

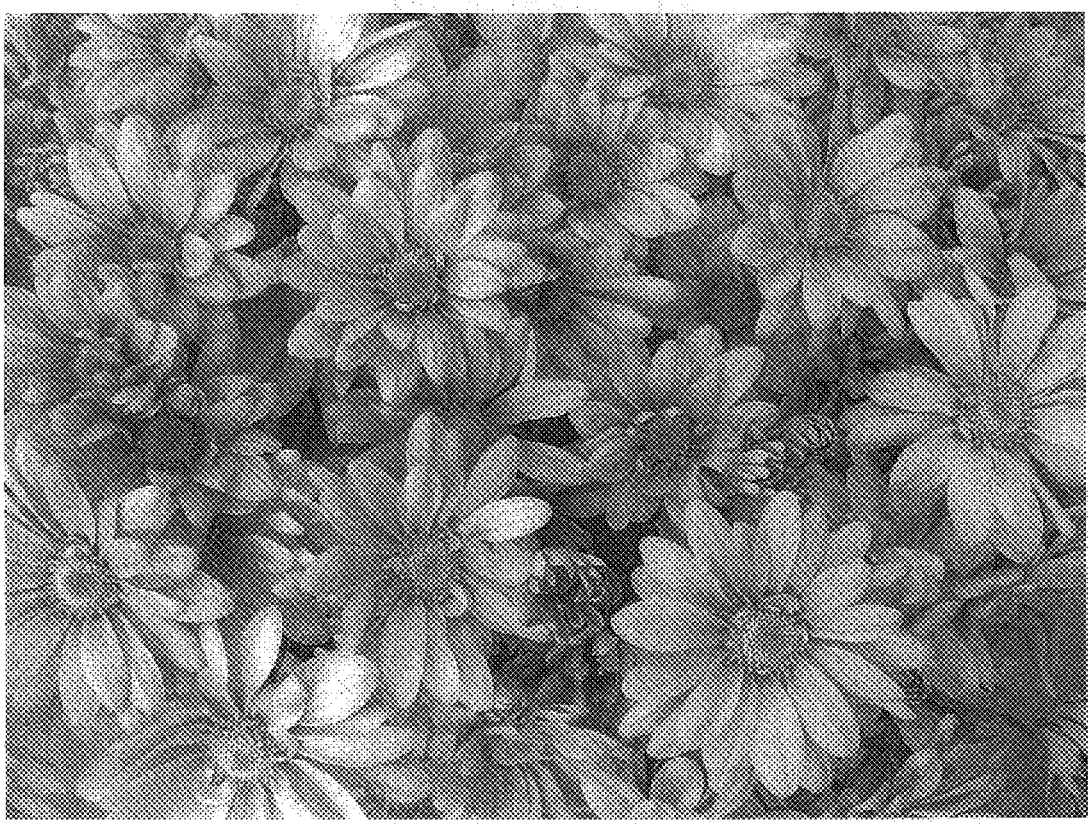

* * * * *